United States Patent
Ouyang et al.

(10) Patent No.: US 6,939,685 B2
(45) Date of Patent: Sep. 6, 2005

(54) STABILIZED TETRAZOLIUM PHENAZINE REAGENT COMPOSITIONS AND METHODS FOR USING THE SAME

(75) Inventors: Tianmei Ouyang, Fremont, CA (US); Paing Huang, San Francisco, CA (US); Xiaoling Zheng, Fremont, CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 09/988,494

(22) Filed: Nov. 20, 2001

(65) Prior Publication Data

US 2003/0096389 A1 May 22, 2003

(51) Int. Cl.$^7$ ............... C12Q 1/26; C12Q 1/32; C12N 9/02; A61K 38/43; A61K 38/44; A01N 59/06
(52) U.S. Cl. ............... 435/26; 435/4; 435/25; 435/183; 435/189; 424/94.1; 424/94.4; 424/682
(58) Field of Search ............... 435/4, 25, 26, 435/183, 189; 424/94.1, 94.4, 682, 9.6, 9.1, 94.2, 657, 658, 659, 660

(56) References Cited

U.S. PATENT DOCUMENTS

| | | | |
|---|---|---|---|
| 4,613,569 A | | 9/1986 | Geisler et al. |
| 4,724,204 A | * | 2/1988 | Steinbach et al. |
| 4,847,196 A | | 7/1989 | Geisler et al. |
| 5,902,731 A | | 5/1999 | Ouyang et al. |
| 6,200,773 B1 | | 3/2001 | Ouyang et al. |

FOREIGN PATENT DOCUMENTS

| | | |
|---|---|---|
| CN | 1317575 A | 10/2001 |
| DE | 2 147 466 | 3/1973 |
| DE | 21 47 466 A | 3/1973 |
| EP | 0 054 689 A | 6/1982 |
| EP | 0330517 A2 | 8/1989 |
| EP | 0908453 A1 | 4/1999 |
| EP | 0654079 B1 | 3/2000 |
| EP | 1130111 A2 * | 9/2001 |
| JP | 1985-070861 * | 2/1985 |
| WO | WO 94/01544 | 1/1994 |
| WO | WO 94/01578 | 1/1994 |

* cited by examiner

Primary Examiner—Leon B. Lankford, Jr.
Assistant Examiner—Ruth A. Davis
(74) Attorney, Agent, or Firm—Carol M. LaSalle; Bozicevic, Fields & Francis LLP

(57) ABSTRACT

Stabilized tetrazolium dye-phenazine reagent compositions and methods for their use in the measurement of an analyte in a sample are provided. The subject reagent compositions include: (1) a tetrazolium dye component, e.g., a water soluble tetrazolium salt; (2) a phenazine component; and (3) an effective amount of one or more tetrazolium dye-phenazine stabilizing reagents, e.g., an inorganic Group IIIA compound and/or a flavin. In many embodiments, the subject reagent compositions include additional members of an analyte oxidizing signal producing system, such as: an analyte oxidizing enzyme, e.g., an analyte dehydrogenase or an analyte oxidase; and an enzyme cofactor. Also provided are test strips that include the subject reagent compositions, as well as systems and kits incorporating the subject test strips. The subject reagent compositions, test strips, systems and kits find use in the detection of a wide variety of analytes in a sample, such as a physiological sample, e.g., blood or a fraction thereof, or ISF (interstitial fluid).

12 Claims, 3 Drawing Sheets

STABILIZED TETRAZOLIUM PHENAZINE REAGENT COMPOSITIONS AND METHODS FOR USING THE SAME

FIELD OF THE INVENTION

The field of this invention is analyte measurement

BACKGROUND OF THE INVENTION

Analyte measurement in physiological fluids, e.g., blood or blood-derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include alcohol, formaldehyde, glucose, glutamic acid, glycerol, beta-hydroxybutyrate, L-lactate, leucine, malic acid, pyruvic acid, steroids, etc. In response to this growing importance of analyte measurement, a variety of analyte measurement protocols and devices for both clinical and home use have been developed.

Many of the protocols and devices that have been developed to date employ a signal producing system to identify the presence of the analyte of interest in a physiological sample, such as blood.

While a variety of such signal producing systems have been developed to date for use in the measurement of a wide variety of different analytes, there continues to be a need for the further development of such systems.

Relevant Literature

Patent documents of interest include: U.S. Pat. Nos. 6,200,773; 5,902,731; 4,613,569, 4,847,196; EP 0 908 453 A1; WO 94/01578 and WO 94/01544.

SUMMARY OF THE INVENTION

Stabilized tetrazolium dye-phenazine reagent compositions that include a tetrazolium dye reagent, e.g., a water soluble tetrazolium salt, and an effective amount of one or more tetrazolium dye-phenazine stabilizing reagents, e.g., an inorganic Group IIIA compound and/or a flavin, are provided. In many embodiments, the reagent compositions include members of analyte oxidizing signal producing system of which the tetrazolium dye and phenazine reagents are members, which system includes one or more of the following additional components: an analyte oxidizing enzyme, e.g., an analyte dehydrogenase or an analyte oxidase; and an enzyme cofactor. Also provided are test strips that include the subject reagent compositions, as well as systems and kits incorporating the subject test strips. The subject reagent compositions, test strips, systems and kits find use in the measurement of a wide variety of analytes in a sample, such as a physiological sample, e.g., blood or a fraction thereof, or ISF (interstitial fluid).

DESCRIPTION OF THE SPECIFIC EMBODIMENTS

Figure 1:
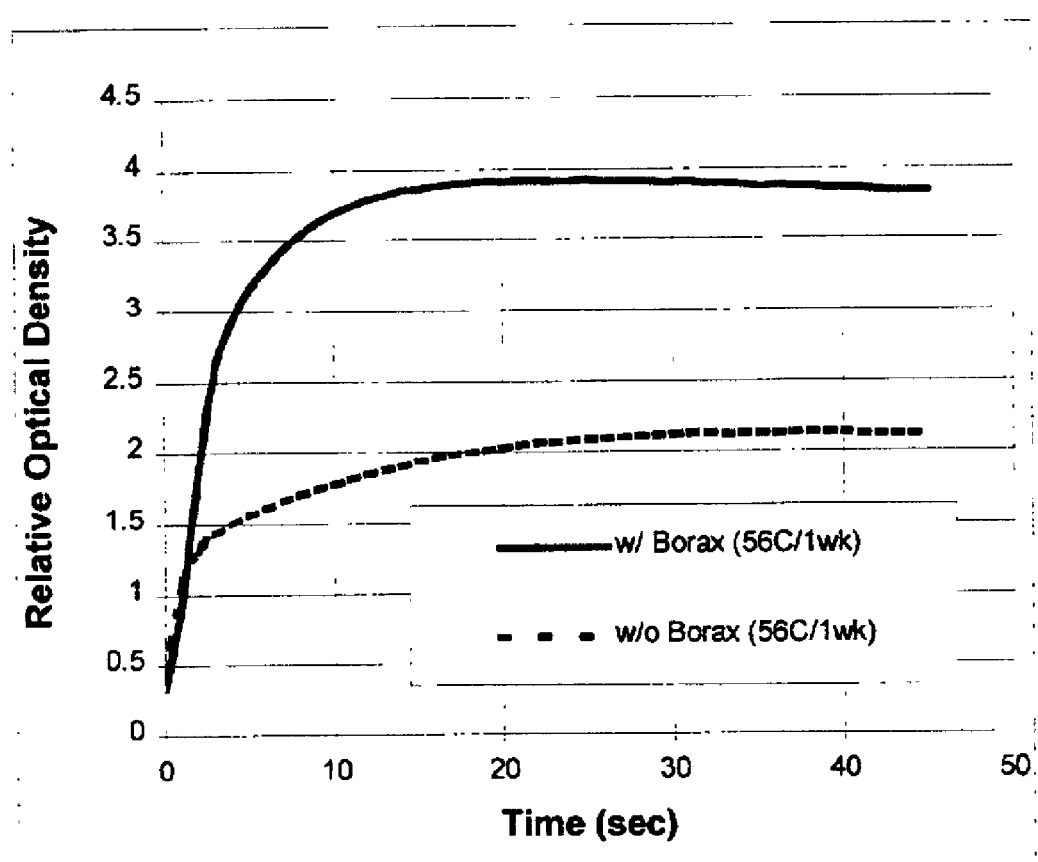
FIG. 1 provides characterization results of a test strip having a reagent composition with and without borax.

Stabilized tetrazolium dye-phenazine reagent compositions and methods for their use in the measurement of an analyte in a sample are provided. The subject reagent compositions include: (1) a tetrazolium dye component, e.g., a water soluble tetrazolium salt; (2) a phenazine component; and (3) an effective amount of one or more tetrazolium dye-phenazine stabilizing reagents, e.g., an inorganic Group IIIA compound and/or a flavin. In many embodiments, the subject reagent compositions include additional members of an analyte oxidizing signal producing system, such as: an analyte-oxidizing enzyme, e.g., an analyte dehydrogenase or an analyte oxidase; and an enzyme cofactor. Also provided are test strips that include the subject reagent compositions, as well as systems and kits incorporating the subject test strips. The subject reagent compositions, test strips, systems and kits find use in the detection of a wide variety of analytes in a sample, such as a physiological sample, e.g., blood or a fraction thereof, or ISF (interstitial fluid).

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies, which are described in the publications, which might be used in connection with the presently described invention.

As summarized above, the subject invention provides stabilized tetrazolium dye compositions and methods for their use, as well as reagent test strips, systems and kits. In further describing the invention, each of these inventive features is discussed in greater detail below.

Reagent Compositions

As summarized above, the subject invention provides stabilized tetrazolium dye-phenazine reagent compositions, which compositions find use in detecting a wide variety of analytes in a sample. The subject tetrazolium dye-phenazine reagent compositions of the present invention are characterized by at least including a tetrazolium dye reagent; a phenazine electron transfer reagent and an effective amount of one or more tetrazolium dye-phenazine stabilizing reagents, e.g., an inorganic Group IIIA compound and/or a flavin.

The tetrazolium dye reagent is a tetrazolium compound (dye precursor) that, upon acceptance of a transferred hydride, forms a colored formazan product. In many embodiments, the tetrazolium dye reagent is a water soluble tetrazolium salt that is capable of accepting a hydride to produce a water soluble, colored formazan product. Water soluble tetrazolium salts of interest include those described in EP 0 908 453, the disclosure of which is herein incorporated by reference. One class of water soluble tetrazolium salts of interest include those described by formula 2 on page 2, lines 35 to 48 of EP 0 908 453. Another class of water soluble tetrazolium salts of interest include those described by formula 1 on page 3, lines 10–25 of EP 0 908 453.

Specific water soluble tetrazolium compounds or salts that are of particular interest include, but are not limited to: 2-(2'benzothiazolyl)-5-styryl-3-(4'-phthalhydrazidyl) tetrazolium (BSPT), 2-benzothiazolyl-(2)-3,5-diphenyl tetrazolium (BTDP), 2,3-di(4-nitrophenyl) tetrazolium (DNP), 2,5-diphenyl-3-(4-styrylphenyl) tetrazolium (DPSP), distyryl nitroblue tetrazolium (DS-NBT), 3,3'-[3,3'-dimethoxy-(1,1'-biphenyl)-4,4'-diyl]-bis[2-(4-nitrophenyl)-5-phenyl(-2H tetrazolium (NBT), 3-(4,5-dimethyl-2-thiazolyl)-2,5-diphenyl-2H tetrazolium (MTT), 2-phenyl-3-(4-carboxyphenyl)-5-methyl tetrazolium (PCPM), tetrazolium blue (TB), thiocarbamyl nitroblue tetrazolium (TCNBT), tetranitroblue tetrazolium (TNBT), tetrazolium violet, (TV), 2-benzothiazothiazolyl-3-(4-carboxy-2-methoxyphenyl)-5-[4-(2-sulfoethylcarbamoyl)phenyl]-2H-tetrazolium (WST-4), and 2,2'-dibenzothiazolyl-5,5'-bis[4-di(2-sulfoethyl) carbamoylphenyl]-3,3'-(3, 3'-dimethoxy-4,4'-biphenylene) ditetrazolium, disodium salt (WST-5). In certain embodiments, the dye compounds is selected from the group of: 2,2'-dibenzothiazolyl-5,5'-bis[4-di(2-sulfoethyl) carbamoylphenyl]-3,3'-(3,3'-dimethoxy-4,4'-biphenylene) ditetrazolium, disodium salt (WST-5); 2-benzothiazolyl-3-(4-carboxy-2-methoxyphenyl)-5-[4-(2-sulfoethylcarbamoyl)phenyl]-2H-tetrazolium (WST-4) and the like. WST-5 is preferred in many embodiments because it readily dissolves in an aqueous medium, which is most compatible with biological samples. Furthermore, the resulting formazan compound exhibits strong spectral absorption at the purple-blue region, thus reducing the need for correcting the background signal from hemoglobin. While the amount of the tetrazolium dye reagent may vary depending on the nature of the reagent composition, e.g., whether it is in dry or wet form, the concentration of the dye reagent in many embodiments ranges from about 1.5 mM to about 50 mM, usually from about 3 mM to about 40 mM and more usually from about 3.5 mM to about 28 mM.

The subject reagent compositions also include a phenazine electron transfer agent. By phenazine electron transfer agent is meant a phenazine compound or molecule that can transfer an electron, in the form of a hydride ion, from a reduced enzyme cofactor to the water soluble tetrazolium product. Specific phenazine compounds of interest include, but are not limited to: phenazine, phenazine methosulfate (PMS), phenazine ethosulfate, methoxyphenazine methosulfate and safranine. While the amount of the phenazine electron transfer reagent may vary depending on the nature of the reagent composition, e.g., whether it is in dry or wet form, the concentration of the phenazine reagent in many embodiments ranges from about 0.01 mM to about 50 mM, usually from about 0.05 mM to about 10 mM and more usually from about 0.1 mM to about 5 mM.

In addition to the tetrazolium dye and phenazine components described above, the subject reagent compositions also include an effective amount of one or more tetrazolium dye-phenazine stabilizing reagents, e.g., an inorganic Group IIIA compound and/or a flavin. As such, in certain embodiments, the subject reagent compositions include an effective amount of a Group IIIA compound. In other embodiments, the subject compositions include an effective amount of a flavin. In yet other embodiments, the subject compositions include effective amounts of both a Group IIIA compound and a flavin. By effective amount is meant an amount sufficient to stabilize the tetrazolium-phenazine system so that it provides a substantially greater optical density signal after at least about 10 sec than a system that does not include the stabilizing agent(s), as measured using the evaluation protocol reported in the Experimental Section, below. An optical density is considered to be substantially greater than a control (where no stabilizing agent is employed) if, at the 10 sec point, it is at least about 2 fold, usually about 2.14 fold greater than the control.

Any convenient Group IIIA compound may be employed which provides for the desired stabilization. Representative Group III compounds are those include elements of the Group IIIA column of the periodic table, e.g., B, Al, Ga, In, Tl, where in many embodiments, the Group IIIA compound is a boron or aluminum compound, where of particular interest are inorganic compounds that include these elements, e.g., borates (or boric acid), aluminates, etc., where in many embodiments the compound is a borate, e.g., borax, or boric acid. The ratio of Group IIIA stabilizing component to tetrazolium dye in the composition typically ranges from about 50 to about 800, usually from about 100 to about 400. As such, in many embodiments, the concentration of the Group IIIA stabilizing reagent in the composition ranges from about 0.1 M to about 1.2 M, usually from about 0.2 M to about 1 M.

Any convenient flavin compound may be employed which provides for the desired stabilization. Representative flavin compounds are FMN and FAD. The ratio of flavin stabilizing component to tetrazolium dye in the composition typically ranges from about 0.02 to about 17, usually from about 0.03 to about 1. As such, in many embodiments, the concentration of the flavin stabilizing reagent in the composition ranges from about 1 mM to about 25 mM, usually from about 2 mM to about 15 mM.

Where both a Group IIIA and flavin stabilizing agent are present in the composition, the ratio of the amounts of these two agents typically ranges from about 2 to about 800, usually from about 10 to about 400.

The presence of the stabilizing agent(s) described above stabilizes the tetrazolium dye-phenazine system, as described above, with respect to heat (56° C.) exposure of at least about one week.

As mentioned above, the subject reagent compositions typically further include additional members of an analyte oxidizing signal producing system. By signal producing system is meant a collection of two or more compounds or molecules which are capable of acting in concert, when combined, to produce a detectable signal that is indicative of the presence of, and often amount of, a particular analyte in a given sample. The term signal producing system is used broadly to encompass both a mixture of all of the reagent constituents of the signal producing system as well as a system in which one or more of the reagent constituents are separated from the remainder of the reagent constituents, e.g., as is present in a kit.

As mentioned above, the signal producing system of the subject compositions is an analyte oxidizing signal producing system. The analyte oxidizing agent is generally an enzyme that is capable of removing a hydride from the analyte of interest to produce an oxidized form of the analyte. Analyte oxidizing enzymes of interest includes analyte oxidases and analyte dehydrogenases. Analyte oxidases of interest include, but are not limited to: glucose oxidase (where the analyte is glucose); cholesterol oxidase (where the analyte is cholesterol); alcohol oxidase (where the analyte is alcohol); bilirubin oxidase (where the analyte is bilirubin); choline oxidase (where the analyte is choline); formaldehyde dehydrogenase (where the analyte is formaldehyde); glutamate oxidase (where the analyte is L-glutamic acid); glycerol oxidase (where the analyte is glycerol); galactose oxidase (where the analyte is galactose); L-ascorbate oxidase (where the analyte is ascorbic acid); lactate oxidase (where the analyte is lactic acid); leucine oxidase (where the analyte is leucine); malate oxidase (where the analyte is malic acid); pyruvate oxidase (where the analyte is pyruvic acid); urate oxidase (where the analyte is uric acid); and the like.

Analyte dehydrogenases of interest include, but are not limited to: alcohol dehydrogenase for alcohol; formaldehyde dehydrogenase for formaldehyde; glucose dehydrogenase for glucose; glucose-6-phosphate dehydrogenase for glucose-6-phosphate; glutamate dehydrogenase for glutamic acid; glycerol dehydrogenase for glycerol; beta-hydroxybutyrate dehydrogenase for beta-hydroxybutyrate; hydroxysteroid dehydrogenase for steroid; L-lactate dehydrogenase for L-lactate; leucine dehydrogenase for leucine; malate dehydrogenase for malic acid, and pyruvate dehydrogenase for pyruvic acid.

In many embodiments, the subject signal producing systems also include an enzyme cofactor that is capable of interacting with the oxidizing agent in a manner such that the analyte of interest is oxidized by the oxidizing agent, which agent concomitantly reduces the enzyme cofactor. Enzyme cofactors of interest include, but are not limited to: i.e., beta-nicotinamide adenine dinucleotide (beta-NAD); beta-nicotinamide adenine dinucleotide phosphate (beta-NADP); thionicotinamide adenine dinucleotide; thionicotinamide adenine dinucleotide phosphate; nicotinamide 1,N6-ethenoadenine dinucleotide; nicotinamide 1,N6-ethenoadenine dinucleotide phosphate; and pyrrolo-quinoline quinone (PQQ); and flavin compounds, FAD, FMN etc. Enzyme cofactors of particular interest that may be included in the subject signal producing systems include: $PQQH_2$, NADH or NAD(P)H.

As indicated above, the subject compositions are present as either wet or dry compositions. By wet composition is meant a fluid composition, typically an aqueous composition. Such compositions find use in various assay configurations, such as cuvette configurations, which are well known in the art. By dry compositions is meant a composition that is not fluid, i.e., in dry form, such as a composition that is substantially free of uncombined water. Such compositions are typically found in reagent test strips, as described in greater detail below.

Reagent Test Strips

Of particular interest in many embodiments of the subject invention are reagent test strips that include the above described dry reagent compositions and are intended for use in measuring the presence or concentration of an analyte in a sample. In particular, the invention provides dry strips for assaying for a particular analyte in whole blood, e.g., beta-hydroxybutyrate, glucose, etc. In the broadest sense, the reagent test strip includes a solid support and a dry reagent composition present thereon, where the dry reagent composition is made up of all of the reagent compounds necessary to produce a detectable signal in the presence of the analyte of interest. In most embodiments of the subject invention, the dry reagent composition present on the subject test strip is one that includes the following members: an analyte oxidizing enzyme, an enzyme cofactor, an electron transfer agent, a water soluble tetrazolium salt, and borate (or boric acid) and/or flavin-stabilizing reagents, where each of these constituent members are described in greater detail above.

In many embodiments, the subject test strips include a membrane test pad that is affixed to a solid support. The support may be a plastic—e.g., polystyrene, nylon, or polyester—or metallic sheet or any other suitable material known in the art. Associated with the test pad, e.g., coated onto the test pad, incorporated into the test pad, etc., is the reagent composition. The strip may also be configured in more complex arrangements, e.g., where the test pad is present between the support and a surface layer, where one or more reagents employed in sample processing may be present on the surface layer. In addition, flow paths or channels may be present on the test strip, as is known in the art. Of interest in many embodiments is the test strip configurations disclosed in U.S. Pat. No. 5,902,731, the disclosure of which is herein incorporated by reference.

In the subject test strips, the dry reagent composition is associated with, e.g., present on or in, a carrier material or substrate. The substrate may be bibulous or non-bibulous. By bibulous is meant a material that exhibits preferential retention of one or more components as would occur, for example, in materials capable of absorbing or "imbibing" one or more components, as occurs in chromatographic separations. Examples of bibulous materials include, but are not limited to: nylon, untreated forms of paper, nitrocellulose and the like which result in chromatographic separation of components contained in liquids, which are passed therethrough.

Alternatively, the substrate may be non-bibulous. Non-bibulous substrates include inert porous matrices, which provide a support for the various members of the signal producing system, described infra, and may have a positive charge. These matrices are generally configured to provide a location for application of a physiological sample, e.g., blood, and detection of the chromogenic product produced by the dye of the signal producing system. As such, the matrix is typically one that is permissive of aqueous fluid flow through it and provides sufficient void space for the chemical reactions of the signal producing system to take place. A number of different porous matrices have been developed for use in various analyte measurement assays, which matrices may differ in terms of materials, pore sizes, dimensions and the like, where representative matrices include those described in U.S. Pat. Nos. 55,932,431; 5,874,099; 5,871,767; 5,869,077; 5,866,322; 5,834,001; 5,800,829; 5,800,828; 5,798,113; 5,670,381; 5,663,054; 5,459,080; 5,459,078; 5,441,894 and 5,212,061; the disclosures of which are herein incorporated by reference. The dimensions and porosity of the test strip may vary greatly, where the matrix may or may not have a porosity gradient, e.g., with larger pores near or at the sample application region and smaller pores at the detection region. In many embodiments, the matrix is configured as a membrane test pad and is affixed to a solid support, where the support may be a plastic (e.g., polystyrene, nylon or polyester) or metallic sheet or any other suitable material known in the art. Of interest in many embodiments are the test strip configurations disclosed in U.S. Pat. Nos. 5,972,294; 5,968,836; 5,968,760; 5,902,731; 5,846,486; 5,843,692; 5,843,691; 5,789,255; 5,780,304; 5,753,452; 5,753,429; 5,736,103; 5,719,034; 5,714,123; 383,550; 381,591; 5,620,863; 5,605,837; 5,563,042; 5,526,120; 5,515,170; 367,109; 5,453,360; 5,426,032; 5,418,142; 5,306,623; 5,304,468; 5,179,005; 5,059,394; 5,049,487; 4,935,346; 4,900,666 and 4,734,360, the disclosures of which are herein incorporated by reference.

Examples of suitable representative test strip configurations are provided in U.S. Pat. Nos. 6,200,733 and 5,902,731, the disclosures of which are herein incorporated by reference.

The subject test strips may be fabricated employing any convenient protocol. One convenient protocol is to contact at least the test pad portion of the strip with an aqueous composition that includes all of the members of the reagent composition that are to be associated with the test pad in the final reagent test strip. Conveniently, the test pad may be immersed in the aqueous composition, maintained therein for a sufficient period of time and then dried, whereby the test pad of the reagent test strip, which has associated therewith the reagent composition, is produced. As stated above, the aqueous composition will include the various members of the reagent composition to be associated with the test pad of the reagent test strip, where the various members are present in amounts sufficient to provide for the desired amounts in the reagent composition that is produced on the test pad. As such, where the electron transfer agent is non-proteinaceous, the concentration of electron transfer agent present in this aqueous composition typically ranges from about 10 to 50,000, usually from about 50 to 10,000 and more usually from about 100 to 5,000 $\mu$M. In other embodiment which containing both non-proteinaceous and proteinaceous electron transfer agents, the concentration of the proteinaceous electron transfer agent present in the aqueous composition typically ranges from about 10 to 10,000, usually from about 50 to 5,000 and more usually from about 100 to 3,000 U/ml. The concentration of tetrazolium dye, e.g., tetrazolium salt, present in the aqueous composition ranges from about 3 mM to 36 mM, usually from about 6 mM to 24 mM. When present, the enzyme cofactor ranges in concentration from about 1.5 mM to 28 mM, usually from about 3.5 mM to 14 mM. Similarly, the analyte oxidizing agent enzyme ranges in concentration from about 100 U to 5000 U, and usually from about 200 U to 4000 U/ml when present. The amount of Group IIIA stabilizing agent, e.g., borax (or boric aid), when present, typically ranges from about 0.1 M to about 1 M, usually from about 0.2 M to about 0.6 M. The amount of flavin stabilizing agent, e.g., FAD, FMN, when present, typically ranges from about 1 mM to about 25 mM, usually from about 2 mM to about 15 mM. See the experimental section, infra, for a more detailed description of a representative method for preparing the subject reagent test strips.

Methods of Analyte Measurement

The above described signal producing systems, reagent compositions and test strips find use in methods of detecting the presence of, and often the amount of, i.e., the concentration of, an analyte in a sample. A variety of different analytes may be detected using the subject methods, where representative analytes include those described above, e.g., alcohol, formaldehyde, glucose, glutamic acid, glycerol, beta-hydroxybutyrate, L-lactate, leucine, malic acid, pyruvic acid, steroids, etc. While in principle, the subject methods may be used to determine the presence, and often concentration, of an analyte in a variety of different physiological samples, such as urine, tears, saliva, and the like, they are particularly suited for use in determining the concentration of an analyte in blood or blood fractions, e.g., blood derived samples, and more particularly in whole blood, ISF (interstitial fluid).

In the subject methods, the sample and the signal producing system are combined into a reaction mixture, the reaction is allowed to proceed for a sufficient period to time to generate a signal indicative of the presence of (and often amount of) analyte in the sample, and the resultant signal is detected and related to the presence of (and often amount of) analyte in the sample. The above steps may take place in a suitable volume containment means, e.g., cuvette, where the reagent composition is a fluid composition. In many embodiments, the above steps take place on a reagent test strip as described supra.

In certain embodiments, a feature of the subject methods is that the detectable signal is made up of a non-washable spot that forms on the surface of the substrate of the strip. The non-washable spot is made up of water soluble formazan product which is tightly bound to the substrate surface such that it cannot be readily removed from the surface under standard washing conditions. By standard washing conditions is meant the conditions experienced by substrate surface in analyte detection assays where unbound component has to be removed from the surface. An example of standard washing conditions are those employed by those of skill in the art in array based nucleic acid hybridization assays, where non-hybridized nucleic acids are removed from the surface of an array following a hybridization step. Such conditions are well known to those of skill in the art. As such, a feature of the subject methods is the production of a non-washable spot on the surface of the positively charged substrate, where the non-washable spot is made up of the water soluble formazan product.

In practicing many embodiments of the subject methods, the first step is to apply a quantity of the physiological sample to the test strip, where the test strip is described supra. The amount of physiological sample, e.g., blood that is applied to the test strip may vary, but generally ranges from about 2 $\mu$L to 40 $\mu$L, usually from about 5 $\mu$L to 20 $\mu$L. Because of the nature of the subject test strip, the blood sample size that is applied to the test strip may be relatively small, ranging in size from about 2 $\mu$L to 40 $\mu$L, usually from about 5 $\mu$L to 20 $\mu$L. Where blood is the physiological sample, blood samples of a variety of different hematocrits may be assayed with the subject methods, where the hematocrit may range from about 20% to 65%, usually from about 25% to 60%.

Following application of the sample to the test strip, the sample is allowed to react with the members of the signal producing system to produce a detectable product, i.e., the non-washable spot, that is present in an amount proportional to the initial amount of the analyte of interest present in the sample. The amount of detectable product, i.e., signal produced by the signal producing system in the form of the non-washable spot, is then determined and related to the amount of analyte in the initial sample. In certain embodiments, automated instruments that perform the above mentioned detection and relation steps are employed. The above described reaction, detection and relating steps, as well as instruments for performing the same, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,902,731; 5,968,836 and 5,972,294; the disclosures of which are herein incorporated by reference. In the relation step, the derived analyte concentration takes into account the constant contribution of competing reactions to the observed signal, e.g., by calibrating the instrument accordingly.

Also provided by the subject invention are kits for use in practicing the subject methods. The kits of the subject invention at least include a signal producing system as described above, where the signal producing system components may be combined into a single reagent composition or separated, e.g., present in separate containers. In certain embodiments, the signal producing system will be present in the kits in the form of a reagent test strip, as described supra. The subject kits may further include a means for obtaining a physiological sample. For example, where the physiological sample is blood, the subject kits may further include a means for obtaining a blood sample, such as a lance for sticking a finger, a lance actuation means, and the like. In addition, the subject kits may include a control solution or standard, e.g. an analyte control solution that contains a standardized concentration of analyte. In certain embodiments, the kits also include an automated instrument, as described above, for detecting the amount of product produced on the strip following sample application and relating the detected product to the amount of analyte in the sample.

In addition to above mentioned components, the subject kits typically further include instructions for using the components of the kit to practice the subject methods with the subject devices. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

EXAMPLE 1

A 0.8 μm nylon membrane obtained from Pall Corporation (East Hills, N.Y.) was dipped into the reagent of Table 1, until saturated. The excess reagent was scraped off gently with a glass rod. The resulting membrane was hung to dry in a 56° C. oven for 10 minutes. (Porex (0.6 mm thick) was soaked in the nitrite solution of Table 2 and then hung to dry in a 100° C. oven for ten hours. Finally, the membrane was laminated between a polyester stock (0.4 mm Melenex® polyester from ICI America, Wilmington, Del.) and the nitrite-impregnated Porex.)

Table 2 and Porex are not needed if Table 1 contains $NaNO_2$.

TABLE 1

Reagent for a Glucose Test Pad

| Components | Quantity |
|---|---|
| Water | 100 ml |
| (2-[-Morpholino]ethanesulfonic acid) sodium salt MES (MW 217.2, Sigma, St. Louis, MO, USA) Adjust pH to 5–7 by adding 6 M HCl) | 0.8–2.2 gm |
| Borax (MW 381.4, Sigma, St. Louis, MO, USA | 2–4 gm |
| Gantrez 6% (Gantrez AN-139 (Poly Methylvinylether-alt-Maleic Anhydride, MW 1080000, Cat # 41632-0, Aldrich Chemicals Milwaukee, WI USA) Make 6% Gantrez in water, heat to 95° C. for less than 45 min. to get Gantrez 6% which is ready for use). Adjust pH to 5.5–7 by adding 50% NaOH | 2–4 gm |
| Triton X-305 (BASF Corporation, Mount Olive, NJ, USA) | 0.5 to 2 gm. |
| Mannitol (MW 182, Sigma, St. Louis, MO, USA) Adjust pH to 5.5–7 by adding 50% NaOH | 1–10 gm |
| Sodium Nitrite (MW 69, Aldrich Chemicals, Milwaukee, WI USA) | 1–5 gm.* |
| Phenazine Ethosulfate (PES, MW 334.4, Sigma, St. Louis, MO, USA | 100–1000 mg |
| WST-5 (MW 1331.37, Dojindo Laboratory, Japan) | 0.8–4 gm |
| Glucose Oxidase (GO, TOYOBO) | 100–1000 KU |
| Flavin Adenine Dinucleotide (FAD) | 0.2–1 gm |

*If $NaNO_2$ is in Table 1, Table 2 is not needed. If $NaNO_2$ is not in Table 1, Table 2 is needed.

TABLE 2

Nitrite Reagent

| Components | Quantity |
|---|---|
| 10 mM Phosphate Buffer Saline, pH 7.4, (P-3813, Sigma, St. Louis, MO, USA) | 70 ml |
| Ethanol | 30 ml |
| Sodium Nitrite (MW69, Aldrich Chemicals, Milwaukee, WI, USA) | 5 gm |
| Polyvinylpyrrodine (MW 40,000, Sigma, St. Louis, MO, USA) | 200 mg |

FIG. 1. With and without Borax, after stressed at 56° C. for 1 week, tested with blood of 60% HCT and 370 mg/dL Glucose.

Figure 2:
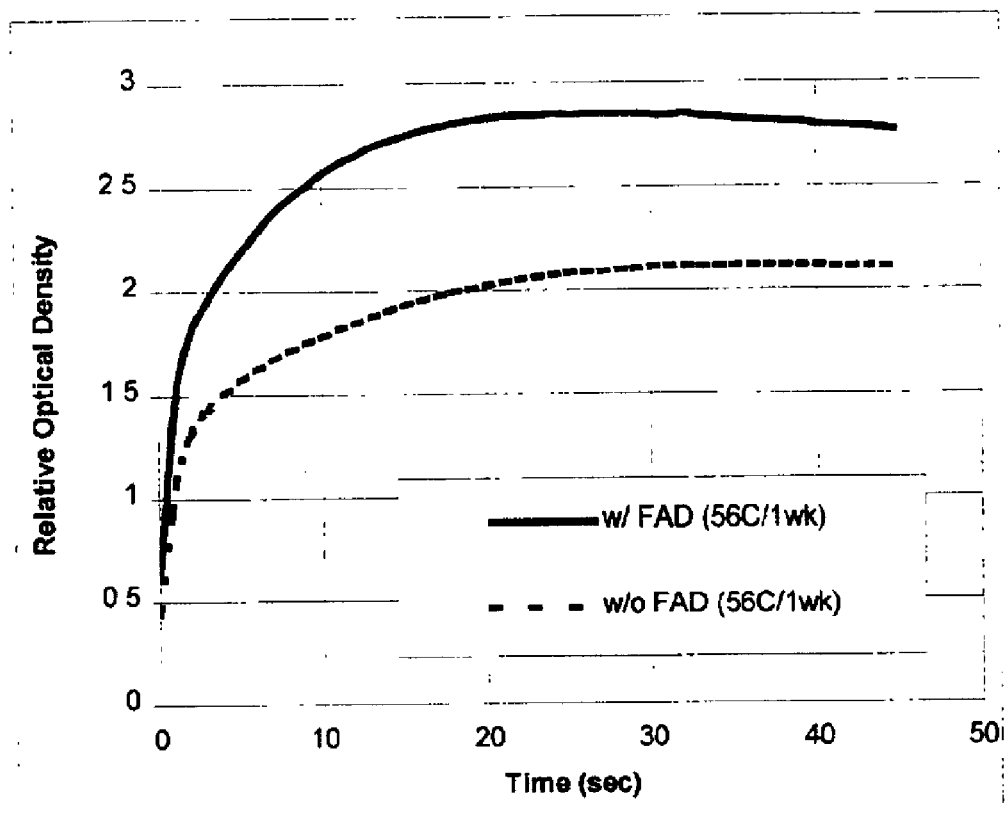
FIG. 2 provides characterization results of a test strip having a reagent composition with and without FAD.

FIG. 2. With and without FAD, after stressed at 56° C. for 1 week, tested with blood of 60% HCT and 370 mg/dL Glucose.

Figure 3:
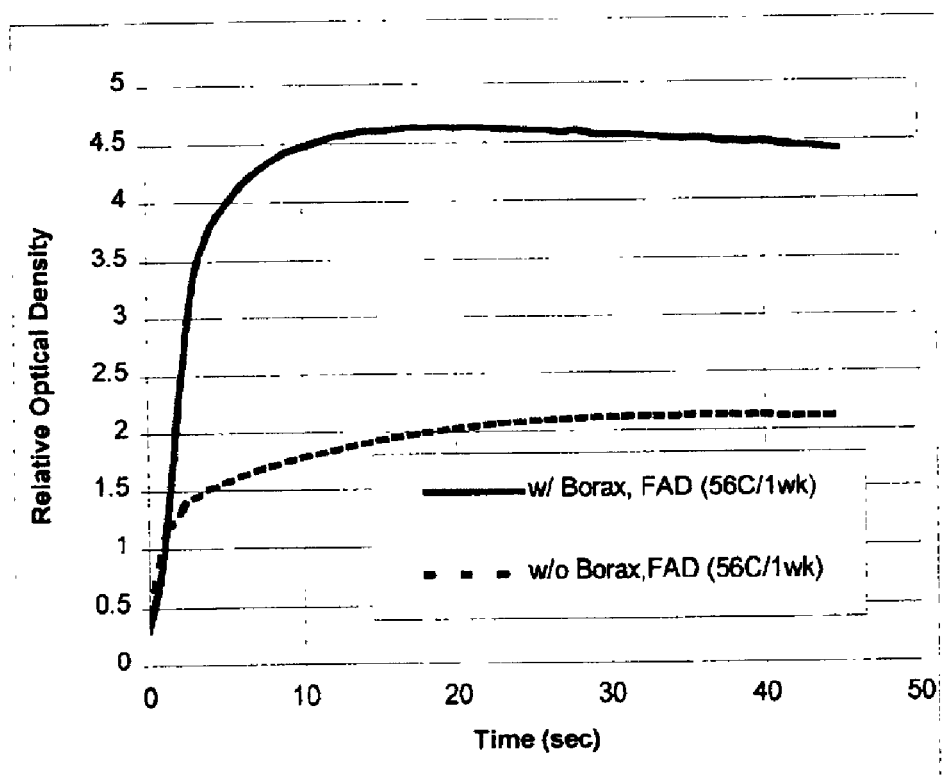
FIG. 3 provides characterization results of a test strip having a reagent composition with and without borax and FAD.

FIG. 3 with and without Borax and FAD, after stressed at 56° C. for 1 week, tested with blood of 60% HCT and 370 mg/dL Glucose.

It is evident from the above results and discussion that the subject invention provides for improvement over previous tetrazolium dye-phenazine reagent compositions, in that it provides for a convenient way to stabilize the dye-electron transfer agent component of the system so that light and/or heat exposure does not adversely effect the dye. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A reagent composition comprising:
   an aluminum compound;
   a tetrazolium dye;
   a phenazine electron transfer agent; and
   a flavin agent present at a concentration that ranges from about 1 mM to about 25.

2. The composition according to claim 1, wherein said flavin agent is flavin adenine dinucleotide (FAD).

3. The composition according to claim 1, wherein said reagent composition comprises an analyte oxidizing signal producing system.

4. The composition according to claim 3, wherein said analyte oxidizing signal producing system comprises an analyte oxidase.

5. The composition according to claim 3, wherein said analyte oxidizing signal producing system comprises an analyte dehydrogenase.

6. The composition according to claim 1, wherein said phenazine agent is phenazine ethosulfate (PES).

7. The composition according to claim 3, wherein said analyte oxidizing signal producing system further comprises an enzyme cofactor.

8. The composition according to claim 1, wherein said aluminum compound and said tetrazolium dye are present at a molar ratio of about 50 to about 800.

9. The composition according to claim 1, wherein aluminum compound and said flavin agent are present a molar ratio of about 2 to about 800.

10. The composition according to claim 1, wherein said aluminum compound is present at a concentration that ranges from about 0.1 M to about 1.2 M.

11. The composition according to claim 1, wherein said tetrazolium dye is present at a concentration that ranges from about 1.5 mM to about 50 mM.

12. The composition according to claim 1, wherein said phenazine electron transfer agent is present at a concentration that ranges from about 0.01 mM to about 50 mM.

* * * * *

UNITED STATES PATENT AND TRADEMARK OFFICE
CERTIFICATE OF CORRECTION

PATENT NO.    : 6,939,685 B2
DATED         : September 6, 2005
INVENTOR(S)   : Ouyang et al.

It is certified that error appears in the above-identified patent and that said Letters Patent is hereby corrected as shown below:

Column 6,
Line 55, "55,932,431" should be -- 5,932,431 --.

Column 7,
Line 34, "embodiment which containing" should be -- embodiments which contain --.

Column 12,
Line 11, "present a molar" should be -- present in a molar --.

Signed and Sealed this

Fourteenth Day of February, 2006

JON W. DUDAS
*Director of the United States Patent and Trademark Office*